United States Patent
Izvoztchikov et al.

(10) Patent No.: US 6,413,767 B1
(45) Date of Patent: Jul. 2, 2002

(54) DEVICE FOR THE PROCESSING AND INFILTRATION OF HISTOLOGICAL SPECIMENS

(76) Inventors: Ilia Borisovitch Izvoztchikov, ul.J.Duclo/d.8,k.2,kv.18, RU-194223 St. Petersburg (RU); James McCormick, 2810 W. Foster Ave., Chicago, IL (US) 60625; Valery Abramovitch Khokhlov, 2-nd Murinsky pr.,d.39,kv.60, RU-194201 St. Petersburg (RU)

( * ) Notice: Subject to any disclaimer, the term of this patent is extended or adjusted under 35 U.S.C. 154(b) by 0 days.

(21) Appl. No.: 09/380,232
(22) PCT Filed: Feb. 27, 1998
(86) PCT No.: PCT/RU98/00053
§ 371 (c)(1), (2), (4) Date: Aug. 30, 1999
(87) PCT Pub. No.: WO98/41837
PCT Pub. Date: Sep. 24, 1998

(30) Foreign Application Priority Data

Mar. 17, 1997 (RU) .......................................... 97104413

(51) Int. Cl.⁷ ................................................. G01N 1/28
(52) U.S. Cl. .................................. 435/286.5; 435/307.1
(58) Field of Search ........................... 435/40.5, 40.52, 435/286.5, 307.1; 118/50, 52, 64, 426, 428, 693; 134/57 R, 92, 95.1, 95.2, 140, 155, 159

(56) References Cited

U.S. PATENT DOCUMENTS

| | | | | | |
|---|---|---|---|---|---|
| 3,435,835 A | * | 4/1969 | Hobbs | ......................... | 134/159 |
| 3,491,778 A | * | 1/1970 | Lehnert et al. | ........... | 134/57 R |
| 4,353,381 A | * | 10/1982 | Winters | ...................... | 134/159 |
| 4,576,796 A | | 3/1986 | McCormick | | |

FOREIGN PATENT DOCUMENTS

| | | |
|---|---|---|
| DE | 30 42 578 C2 | 6/1982 |
| EP | 0 077 477 B1 | 4/1986 |
| EP | 0 269 316 B1 | 8/1991 |

* cited by examiner

Primary Examiner—Matthew O. Savage
(74) Attorney, Agent, or Firm—Paul Vincent

(57) ABSTRACT

The device for processing and infiltration of histological specimens according to the invention applied for comprises a rotating means consisting of a ring of containers for cassettes with histological specimens which is mounted on a horizontal rotation axis in the vertical plane. The inner diameter of the ring is 2–4 times the width of a cassette for histological specimens. The rotating means is located in a case, which is connected to tanks for processing and infiltration fluids and to a vacuum pump through branch pipes. The rotating means is connected to a means for rotating it at variable rate.

8 Claims, 2 Drawing Sheets

DEVICE FOR THE PROCESSING AND INFILTRATION OF HISTOLOGICAL SPECIMENS

BACKGROUND OF THE INVENTION

The present invention relates to examination methods and in particular to devices for preparation of histological specimens for microscopic examination.

In order to prepare histological specimens for microscopic examination the specimens taken for examination are successively subjected to the steps of fixation, e.g. in an aqueous formaldehyde solution, dehydration, clearing, and infiltration with paraffin or another suitable wax. The step of dehydration includes treatment of the fixed specimens with an alcohol reagent of gradually increasing concentration. During the clearing stage the specimens are once or several times treated with a clearing agent, e.g. xylene. Infiltration with paraffin (or another wax) is carried out by likewise repeatedly immersing the dehydrated and cleared specimens in melted paraffin or other wax. Only after the above processing steps have been completed a histological specimen is ready for microtoming.

Processing and infiltration of histological specimens may be carried out and often are carried out manually. In this case a lab assistant immerses cassettes with histological specimens in a vessel, adds the required fluids, agitates the vessel, pours away the fluids, places the vessel with the cassettes or the cassettes in a heating or cooling device etc. Manual processing and infiltration of histological specimens is quite labor-intensive and requires qualified staff, while the results obtained are not always reproducible. Laboratories that are specialized in histological examination use automated processing and infiltration devices.

The device for processing and infiltration of histological specimens according EP 0269316 is a multi-chamber apparatus comprising 12 chambers, which are arranged to form a circle, and a means for lifting the container with the specimen holding cassettes and moving them from one chamber to the next. The means is placed on an axis which is connected to a drive located inside the circle of chambers. The circle of chambers has a common cover with an openable opening over each chamber. The means for moving the container is encased. The device is processor-controlled. Cassettes with specimens are inserted in the container which is hung from the rocker of the means for moving the container inside the case. In the mode entered said means immerses the container with the specimens in each of the chambers containing the required reagents, takes the container out, and moves it to the next chamber.

The device according to EP 0269316 provides automated processing and infiltration of histological specimens, but it is not hermetically sealed what may entail pollution of the air in the laboratory with harmful substances, e.g. xylene; it is also not possible to use vacuum at each processing stage.

The device for processing and infiltration of histological specimens according to EP 0077477 includes a chamber for processing the specimens, several tanks for reagents, which are connected to the chamber by a separate valve system, a vacuum pump and a switchable valve system which is connected to the chamber and controls the direction of the reagent's flow. The valve system and the vacuum pump provide a closed cycle for the exchange of the reagents and gases in the system of the chamber and the tanks for the reagents. The device according to EP 0077477 is automated and is controlled by a processor. The program for processing and infiltration of the histological specimens is executed without intervention of an operator. It is also not necessary to take any precaution when using harmful or toxic fluids.

In the devices as mentioned above processing time for a specimen with each consecutive fluid only depends on the diffusion speed of the displaced fluid from the surface of the specimen. In order to intensify the process stirring devices may be used, which, however, do not provide effective exchange of fluids in the arrangement of the cassettes with the specimens.

The device for processing and infiltration of histological specimens according to German Patent No. 3042578 comprises an incubation chamber, in which in pipe cylinders fluid-permeable containers for histological specimens are vertically arranged one on top of the other. A powerful vertical axial pump in the form of a worm or a plunger is located in the middle of the chamber, it forces the processing and infiltration fluids to circulate in the chamber and to flow downward through the pipe cylinders and the containers with the specimens which are located in these cylinders. The continues flow of the fluids around the specimens as described in German Patent No. 3042578 certainly aids in the intensification of the process, but the suggested arrangement of containers provides only poor efficiency.

The device for processing and infiltration of histological specimens according U.S. Pat. No. 4,576,798 also provides processing and infiltration of specimens in a fluid flow. The device comprises an encased vertical rotation axis located in the circular (in plan) case centrally, and a circular rotor which is located on the axis perpendicular to it; several channels that are tilted by 2–5° from center to periphery are formed on the upper surface of the rotor. Depressions are formed near the peripheral end of each channel, in which are disposed perforated containers for the specimens. A hole from which the channels branch off is formed in the center of the rotor. The channels have their continuation from the depressions for the specimens to the edge of the rotor. The device comprises a means for rotating the axis and the rotor, tanks for processing and infiltration fluids and branch pipes for feeding fluids to the case and removing them from the case. The said fluid feeding branch pipe is directed to the hole.

The dehydrating and clearing fluids and the melted paraffin are supplied from the corresponding tanks to the central hole through the branch pipe; the rotation of the rotor forces the fluids to flow in the channels and around the histological specimens, which are located in the depressions at the periphery of the rotor. Processing in the fluid flow provides improved process efficiency. Prior to changing the processing fluid the motor may be switched to a higher rotation rate for removing the previous fluid by centrifuging; this speeds up processing and makes it more efficient. As metal consumption for each specimen to be treated is quite high and as it is possible to insert only few specimens in the device simultaneously, the device according to U.S. Pat. No. 4,576,796 is not very efficient.

SUMMARY OF THE INVENTION

Applied for is a device for processing and infiltration of histological specimens with high productivity as well as high effectiveness in processing and infiltration.

The device for processing and infiltration of histological specimens according to the present invention comprises a rotating means, which is located in a case and consists of a rotation axis with attached containers for cassettes with histological specimens, a means for rotating said rotation axis at variable speed, tanks for processing and infiltration fluids, which are located outside said case, and branch pipes for feeding said fluids to said case and removing them from said case. Additionally said rotation axis of said rotating means is positioned in said case horizontally, said containers for the cassettes with histological specimens are designed as ring sectors which are arranged to form a ring, whereby the inner diameter of said ring is 2–4 times the width of a cassette for histological specimens, and said ring of containers is mounted on the horizontal axis in the vertical plane.

DESCRIPTION OF THE PREFERRED EMBODIMENT

Figure 1:
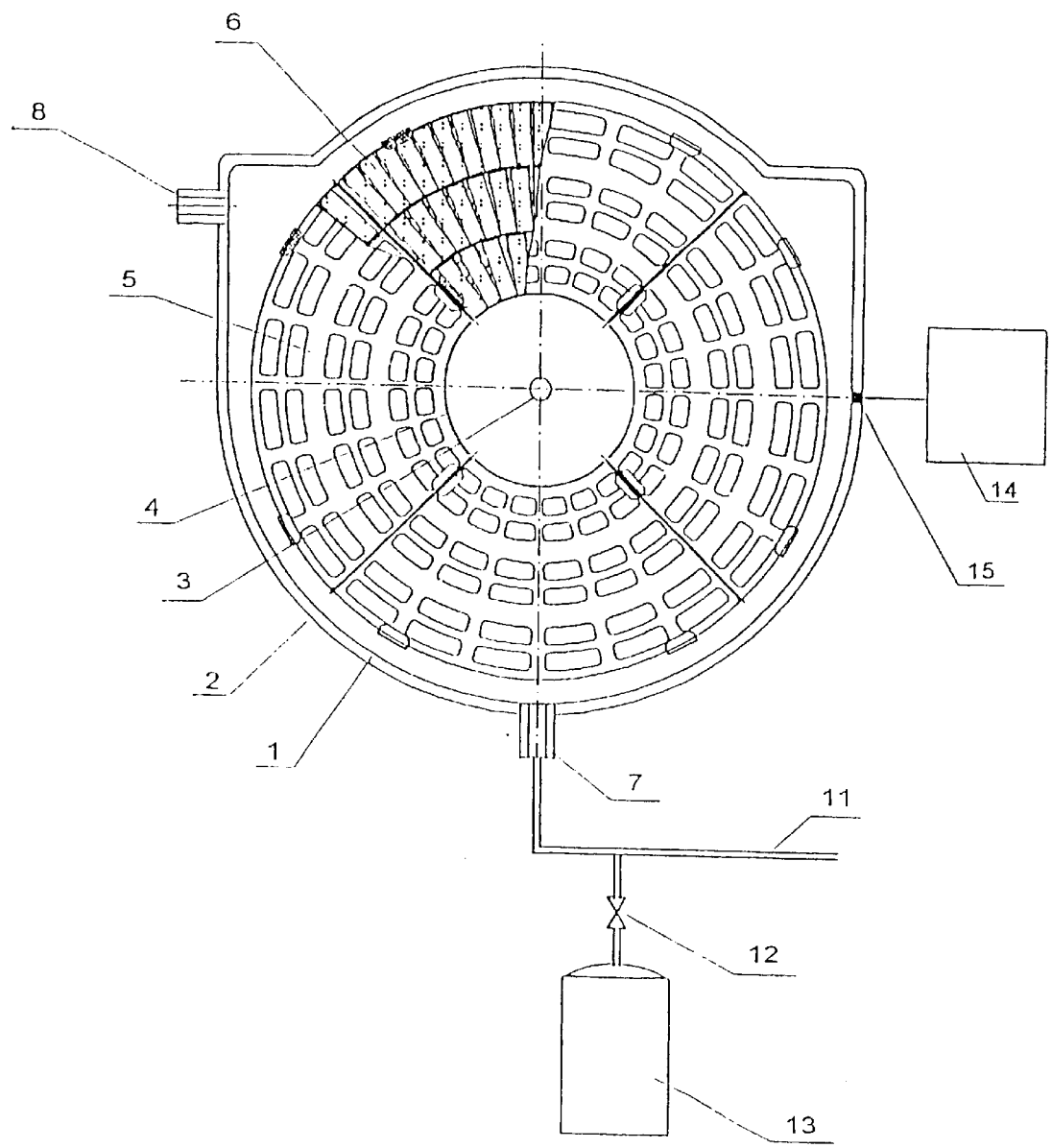
FIG. 1 is a front elevation of the device according to the present invention.
Figure 2:
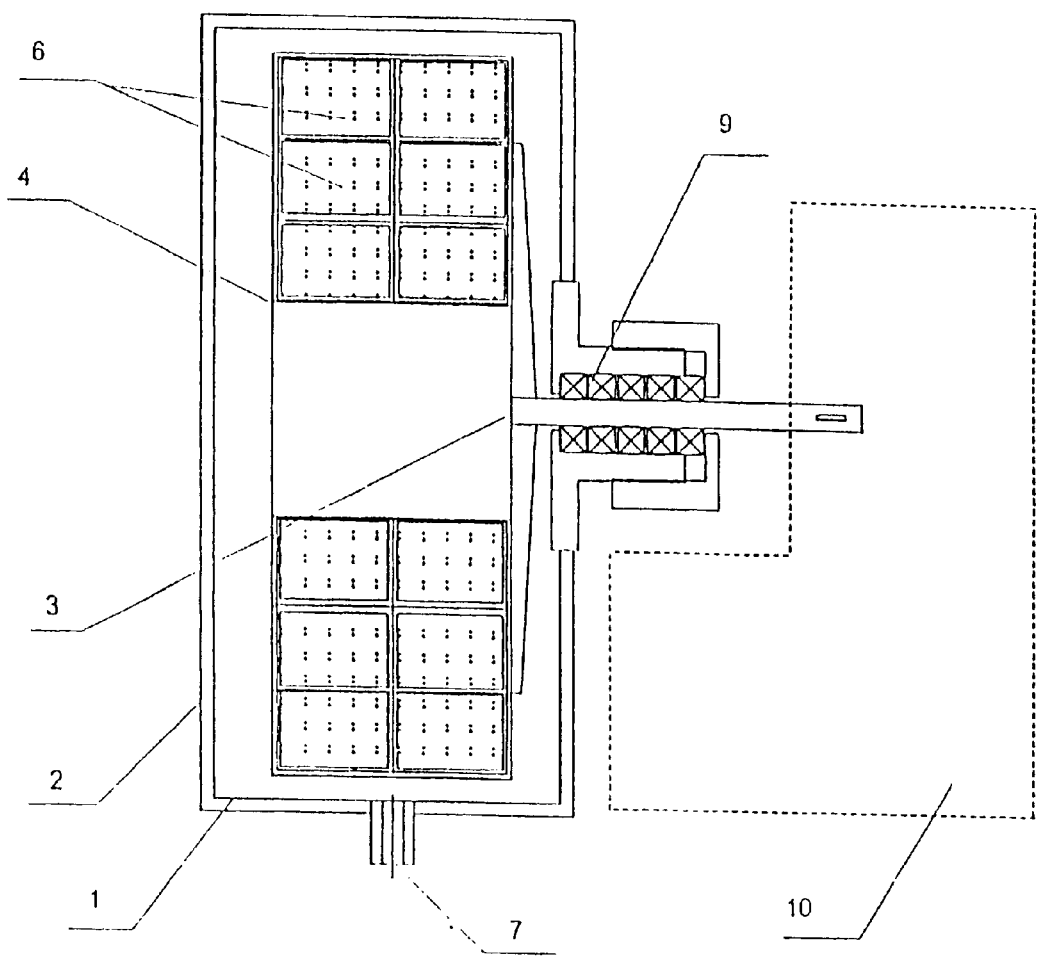
FIG. 2 is a side elevation of the device according to the present invention.

An apparatus according to the present invention as shown in FIGS. 1 and 2 comprises a case 1 with a heat exchanger 2 for heating and cooling the contents. A hollow ring 4 formed by containers 5 is mounted on a horizontal shaft (axis) 3. The number of containers 5 forming the ring may vary between two and twelve; in particular four containers are used, as shown in FIG. 1. Cassettes 6 with histological specimens are disposed in the containers 5. The inner cylinder of the hollow ring 4 has a diameter which is minimum 2 times and maximum 4 times the width of a cassette 6. All surfaces of the containers are perforated.

The case 1 comprises a branch pipe 7 for supplying and removing processing and infiltration fluids and a branch pipe 8 which is connected to a vacuum system (not illustrated). The shaft of the axis 3, which passes through a packing 9 is connected to a variable-speed motor 10.

The branch pipe 7 is connected to a collector 11, which receives the processing or infiltration fluids from tanks 13 through processor-controlled valves 12. The device includes as many tanks 13, connected to the collector 11 through the valves 12, as fluids are necessary for processing and infiltration of the specimens.

The device comprises a means 14 for registering the level of the processing or infiltration fluid in the case 1. The sensor 15 of the means 14 is located on the inner wall of the case 1 as shown in FIG. 1.

The case 1 and all components located in the case 1 as well as the connection pieces are manufactured from a material that is inert to the processing fluids, e.g. from stainless steel. The containers may be manufactured either from perforated sheet or mesh.

The device works as follows:

The tanks 13 are filled with processing and infiltration fluids. The cassettes 6 with histological specimens are inserted in the containers 5. A low vacuum in the range of about 500–600 millimeters of mercury is applied to the case of the apparatus through branch pipe 8. The vacuum forces (sucks up) the first fluid through the valves to the chamber. The level of the processing fluid is set at or above the inner cylinder of the ring and at or below the rotation axis 3; when the sensor responds during the feeding process, feeding is stopped. The motor 10 begins to rotate the shaft 3 and the ring 4 at a rate of 0.1–10 rpm. During rotation the containers are periodically immersed in and taken out of the processing fluid. When the containers are taken out, the processing fluid runs off the containers and the cassettes with the histological specimens. After processing has been completed the fluid is removed from the case and returned to the respective tank 13, the rotation rate of the ring is increased to 5–10 rps in order to remove humidity in the form of drops from the container and the cassettes with the specimens. Processing and centrifuging may be carried out at a residual pressure of about 200–600 millimeters of mercury within the case.

After centrifuging the motor is stopped and the next fluid is fed in the case. These processing steps are repeated for each fluid.

Prior to supplying melted infiltration wax to the case the temperature in the case is increased by the heat exchanger to the melting temperature of the wax in order to maintain the wax in the case in its melted form.

360 cassettes may be simultaneously inserted in the device according to the present invention.

The device may work automatically and is controlled by a processor according to a set program.

The device applied for makes it possible to prepare histological specimens for microscope examination from fixation to infiltration with wax. The periodical immersion of the containers in the processing fluid and the removal of the previous fluid by centrifuging intensify the process and make processing more effective. The possibility of simultaneously inserting a great number of cassettes in the device and the device's effectiveness provide high productivity.

We claim:

1. A device for processing and infiltration of histological specimens disposed in cassettes, the device comprising:

a casing;

a rotation axle extending horizontally into said casing;

containers disposed within said casing and mounted to said rotation axle for rotation thereby, said containers for accepting the cassettes;

means for rotation at variable speed, said rotation means disposed outside said casing and engaging said rotation axle for orientation thereof;

a first tank for holding a first histological specimen treatment fluid selected from a group consisting of a fixing agent, a dehydration agent, a clearing agent, and an infiltration agent;

a second tank for holding a second histological specimen treatment fluid selected from said group consisting of said fixing agent, said dehydration agent, said clearing agent, and said infiltration agent;

a collector pipe member connected between said casing and said first tank and connected between said casing and said second tank;

a first pipe member connected between said first tank and said collector pipe member;

a first valve disposed in said first pipe member;

a second pipe member connected between said second tank and said collector pipe member; and a second valve disposed in said second pipe member, wherein said collector pipe member, said first pipe member, said first valve, said second pipe member, and said second valve cooperate for selective, separate feeding and draining of each of said first and said second treatment fluids to and from said casing.

2. The device of claim 1, wherein said containers are shaped as annular segments disposed about said rotation axle.

3. The device of claim 2, wherein said containers are perforated.

4. The device of claim 2, wherein said containers are disposed to form a ring.

5. The device of claim 4, wherein said ring has an inner diameter which is 2 to 4 times a width of a cassette for histological specimens.

6. The device of claim 4, wherein said containers are mounted on said rotation axle in a plane perpendicular to said rotation axle.

7. The device of claim 4, further comprising a fluid level sensor disposed on a wall of said casing at a height which is lower than a center of said rotational axle and higher than a lower point of an inner cylinder of said ring.

8. A device for processing and infiltration of histological specimens disposed in cassettes, the device comprising:

a rotation axle extending horizontally into a casing;

containers disposed within said casing and mounted to said rotation axle for rotation thereby, said containers for accepting the cassettes, said containers being shaped as annular segments disposed about said rotation axle and arranged to form a ring, said ring having an inner diameter which is 2 to 4 times a width of a cassette, said ring mounted to said rotation axle in a vertical plane;

means for rotation at variable speed, said rotation means disposed outside said casing and engaging said rotation axle for rotation thereof;

a first tank for holding a first histological specimen treatment fluid selected from a group consisting of a fixing agent, a dehydration agent, a clearing agent, and an infiltration agent;

a second tank for holding a second histological specimen treatment fluid selected from said group consisting of said fixing agent, said dehydration agent, said clearing agent and said infiltration agent;

a collector pipe member connected between said casing and said first tank and connected between said casing and said second tank;

a first pipe member connected between said first tank and said collector pipe member;

a first valve disposed in said first pipe member;

a second pipe member connected between said second tank and said collector pipe member; and a second valve disposed in said second pipe member, wherein said collector pipe member, said first pipe member, said first valve, said second pipe member, and said second valve cooperate for selective, separate feeding and draining of each of said first and said second treatment fluids to and from said casing.

* * * * *